(12) United States Patent
Tomura et al.

(10) Patent No.: US 6,212,251 B1
(45) Date of Patent: Apr. 3, 2001

(54) HELICAL SCANNING TYPE X-RAY CT APPARATUS WITH MOVABLE GANTRY

(75) Inventors: Masatoshi Tomura; Naofumi Watanabe; Yasuo Kodaira; Yasuhiro Seki, all of Tochigi (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/203,493

(22) Filed: Dec. 2, 1998

(30) Foreign Application Priority Data

Dec. 3, 1997 (JP) .................................................. 9-333232

(51) Int. Cl.⁷ .................................................. A61B 6/00
(52) U.S. Cl. .................. 378/15; 378/4; 378/17; 378/195
(58) Field of Search .................. 378/4, 11, 15, 378/17, 195

(56) References Cited

U.S. PATENT DOCUMENTS

| 5,448,607 | 9/1995 | McKenna ................................. 378/4 |
| 5,740,222 | 4/1998 | Fujita et al. ............................. 378/62 |
| 5,748,696 | 5/1998 | Fujita et al. ............................. 378/4 |

OTHER PUBLICATIONS

Phillips Catalog, Tomoscan M, CT System, 10 pages.

*Primary Examiner*—David V. Bruce
*Assistant Examiner*—Daniel S Felten
(74) *Attorney, Agent, or Firm*—Oblon, Spivak, McClelland, Maier & Neustadt, P.C.

(57) ABSTRACT

A helical-scanning type of X-ray CT apparatus includes a dolly 15 and a gantry body 7 mounted on the dolly 15. The dolly 15 is capable of translation relatively to a patient 5 lying on a tabletop 3. An X-ray tube 9 and an X-ray-detector 11 opposing the X-ray tube 9 are rotatably accommodated in the gantry body 7. In operation, the helical scanning operation of the X-ray CT apparatus is carried out by combining the translation of the dolly 15 with the rotation of the X-ray tube 9.

10 Claims, 5 Drawing Sheets

HELICAL SCANNING TYPE X-RAY CT APPARATUS WITH MOVABLE GANTRY

BACKGROUND OF THE INVENTION

1. Field of the Invention

The present invention relates generally to a helical-scanning type of X-ray CT apparatus which scans an object to be scanned in a helical manner and, more particularly, to a helical-scanning type of X-ray CT apparatus which carries out the helical scanning for the object to be scanned by means of a movable gantry, without moving the object to be scanned.

2. Description of the Related Art

In the conventional helical-scanning type of CT apparatus, a table top of a patient couch mounting the object to be scanned thereon is continuously moved at a regular speed in a X-ray CT gantry dome including, for example, a X-ray tube and a detector both rotating continuously, so that a helical movement of a scanning section relative to the object to be scanned can be accomplished.

Recently, with the broad field of medical treatments with the application of the X-ray CT apparatus, there are demands for executing the X-ray CT scanning during a surgical operation for brain and inspecting while taking an angiography unit and the X-ray CT apparatus together in the interventional radiology (IVR) technique where a puncturing, an exploratory excision and a catheter handling are carried out with reference to the radiographic image of the object to be scanned.

However, it should be noted that there is raised the following problem in the application of the conventional X-ray CT apparatus to the field of medical treatment.

For example, in case of executing such an X-ray CT scanning during the brain surgical operation, it should be recognized a patient couch mounting the patient thereon is a table for surgical operation. It is general that the table for surgical operation is required to have a function of allowing the patient to be fixed into a desirable posture for the operation.

For example, in the brain surgical operation, the table is required to have a function of maintaining the patient's semi-sitting posture (i.e. Fowler position) where the only upper body of the patient is raised by 40 to 50 cm. Therefore, it is difficult in technique to allow the table for operation to have a function of feeding a tabletop for helical scanning.

Note, although there has been provided a patient couch which is commonly usable for the angiography unit and X-ray CT apparatus in the interventional radiology (IVR) technique, the patient couch has a problem of making a free manipulation for a tabletop heavier since the angiography unit is required to have a function of allowing the tabletop to be moved back, forth, right and left freely, while the X-ray CT apparatus is required to have a function of feeding the tabletop precisely for the helical scanning,

SUMMARY OF THE INVENTION

It is therefore an object of the present invention to provide a helical-scanning type of X-ray CT apparatus which is capable of scanning the object to be scanned without moving the object.

Another object of the present invention is to provide a helical-scanning type of X-ray CT apparatus which is capable of scanning the object mounted on a tabletop or a surgical table etc. each of which has no function of feeding the tabletop.

To achieve the objects described above, there is provided a helical-scanning type of X-ray CT apparatus comprising:
- a CT gantry having an X-ray source for irradiating an X-ray while rotating about an object to be scanned and an X-ray detector for detecting the X-ray penetrating through the object to be scanned;
- a moving unit for continuously moving the CT gantry with respect to the object to be scanned; and
- a detector for detecting a moving distance of the CT gantry.

According to the invention, the helical scanning for the object to be scanned can be accomplished by moving the CT gantry in succession while rotating the X-ray source about the object to be scanned.

In the above-mentioned constitution, preferably, the moving unit comprises a dolly which mounts the CT gantry thereon and is capable of moving in a horizontal direction, while a rotating plane of the X-ray source is generally vertical. In this case, the helical scanning operation of the X-ray CT apparatus is carried out by combining a translation (horizontal movement) of the dolly with the rotation of the X-ray source.

Alternatively, it is also preferable that the moving unit comprises
- a dolly which is movable together with the CT gantry and a sliding table which mounts the CT gantry thereon and is capable of moving continuously with respect to the dolly. In this case, the helical scanning operation of the X-ray CT apparatus is carried out by combining the continuous movement of the sliding table with the rotation of the X-ray source.

In the above-mentioned present invention, preferably, the moving unit comprises:
- a first driving unit for positioning the CT gantry in a rough-and-ready manner;
- a second driving unit for moving the CT gantry strictly for helical-scanning; and
- a switching unit which switches the operations of the first and second driving units so that either one of the first and second driving units does operate solely.

With the above-mentioned arrangement, it is possible to rapidly bring the X-ray CT apparatus near the object to be scanned by the first driving unit and precisely move the CT gantry for helical scanning by the second driving unit.

Alternatively, for the same purpose, the moving unit may comprise:
- a single drive motor; and
- a changing unit which is capable of changing a rotating speed of the single drive motor by changing any one of voltages, currents, frequency, pulse frequency all supplied for the single drive motor and motor windings to which power is applied.

In the X-ray CT apparatus, more preferably, the dolly is provided with at least one safety switch for detecting that the dolly comes into contact with an external object which is not a constituent of the X-ray CT apparatus.

In this case, owing to the provision of the safety switch, it is expected to prevent the dolly and the external object from being damaged seriously.

Similarly, it is also preferable that the CT gantry is provided, on a front side thereof close to the object to be scanned, with at least one safety switch for detecting that the CT gantry comes into contact with an external object which is not a constituent of the X-ray CT apparatus.

Also in this case, owing to the provision of the safety switch, it is expected to prevent the CT gantry and the external object from being damaged seriously.

Similarly, it is also preferable that the CT gantry is provided, on an inner wall defining a radiographic port thereof, with a safety switch which can detect that the CT gantry comes into contact with the object to be scanned.

In such a case, owing to the provision of the safety switch, it is expected to prevent the object to be scanned from taking contact with the CT gantry intensely.

In the above arrangement, more preferably, the safety switch is in form of a mat switch of which sensitive part includes material for cushioning the object to be scanned against a contact thereof with the CT gantry.

In this case, it is possible to soften the shock of the object to be scanned and the external object with the CT gantry furthermore.

Alternatively, in place of the above safety switches, the moving unit may includes a control unit which controls the dolly in such a manner that once the positioning of the dolly prior to the helical scanning is completed, thereafter the dolly can be only traveled in one direction receding from the object to be scanned. In this case, since the dolly after being positioned does not approach the object any more, it is possible to exclude the possibility of contact of the dolly with the object.

These and other objects and features of the present invention will become more fully apparent from the following description and appended claims taken in conjunction with the accompany drawing.

BRIEF DESCRIPTION OF THE DRAWINGS

FIGS. 4A to 4C show the X-ray CT apparatus equipped with a sliding table, in accordance with a second embodiment of the present invention, in which

DESCRIPTION OF THE PREFERRED EMBODIMENT

Figure 1:
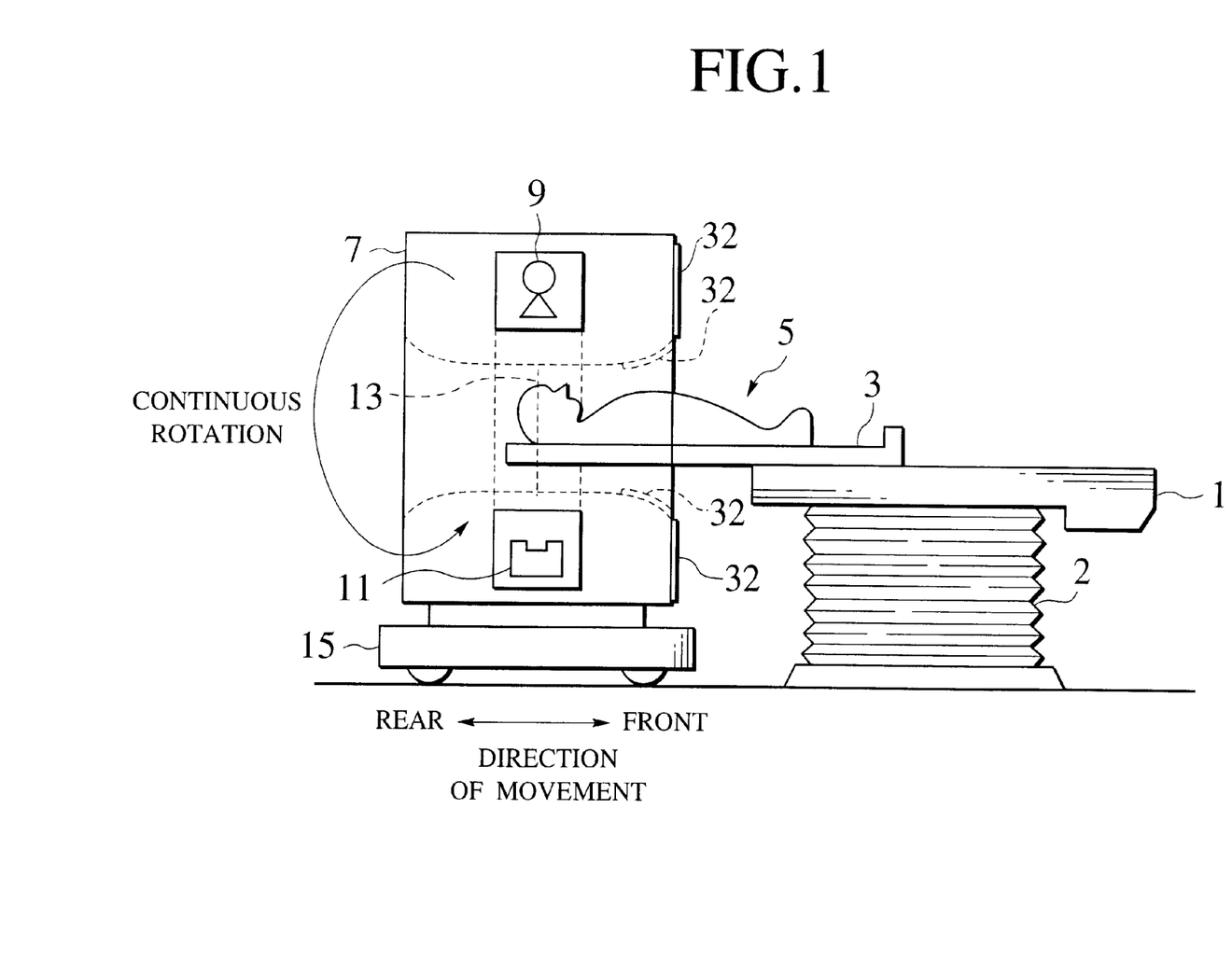
FIG. 1 schematic view of a helical scanning type of X-ray CT apparatus including a movable gantry of the present invention, showing the principle of operation.

First of all, we now describe the principle of the present invention, with reference to FIG. 1. FIG. 1 shows a patient 5 as an object to be scanned, who is lying on a tabletop 3 of a patient couch 1. The tabletop 3 of the patient couch 1 is not equipped with a tabletop feeding arrangement for helical scanning, different from that of the conventional X-ray CT apparatus and therefore, the patient 5 is fixed on the tabletop 3 during the helical scanning. An X-ray CT gantry body 7 is provided with an X-ray tube 9 as a source of X-ray and an X-ray detector 11 opposing the X-ray tube 9. Both of the X-ray tube 9 and the X-ray detector 11 are accommodated in the gantry body 7 so as to successively rotate about a scanning area 13. The gantry body 7 is mounted on a dolly 15 which is continuously movable in the horizontal direction corresponding to right and left of the drawing.

Consequently, owing to the combination of continuous rotating of the X-ray tube 9 with the continuous translation (horizontal movement) of the dolly 15, the X-ray CT apparatus of the invention is capable of scanning the patient 5 in a helical manner.

Thus, according to the present invention, since there is no need of continuously moving the object to be scanned for the helical scanning, it is not necessary that the patient couch mounting the object thereon has a function of precisely feeding the tabletop for the helical scanning. It means that in the X-ray CT apparatus of the invention, the helical-scanning X-ray CT tomography can be completed while making use of an operation table having no function of feeding the tabletop.

Embodiments of the invention will be described as follow.

Figure 2:
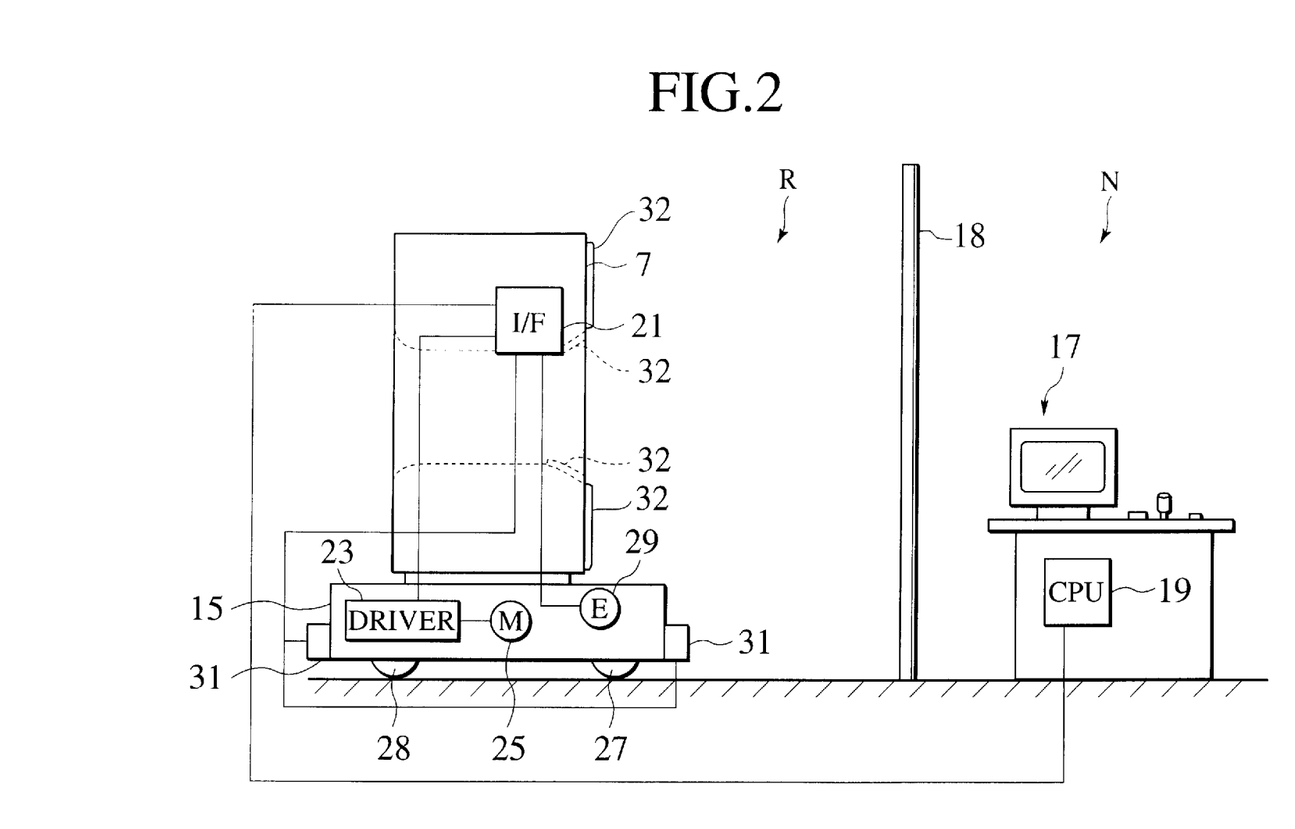
FIG. 2 is a schematic block diagram of the X-ray CT apparatus of the present invention.
Figure 3:
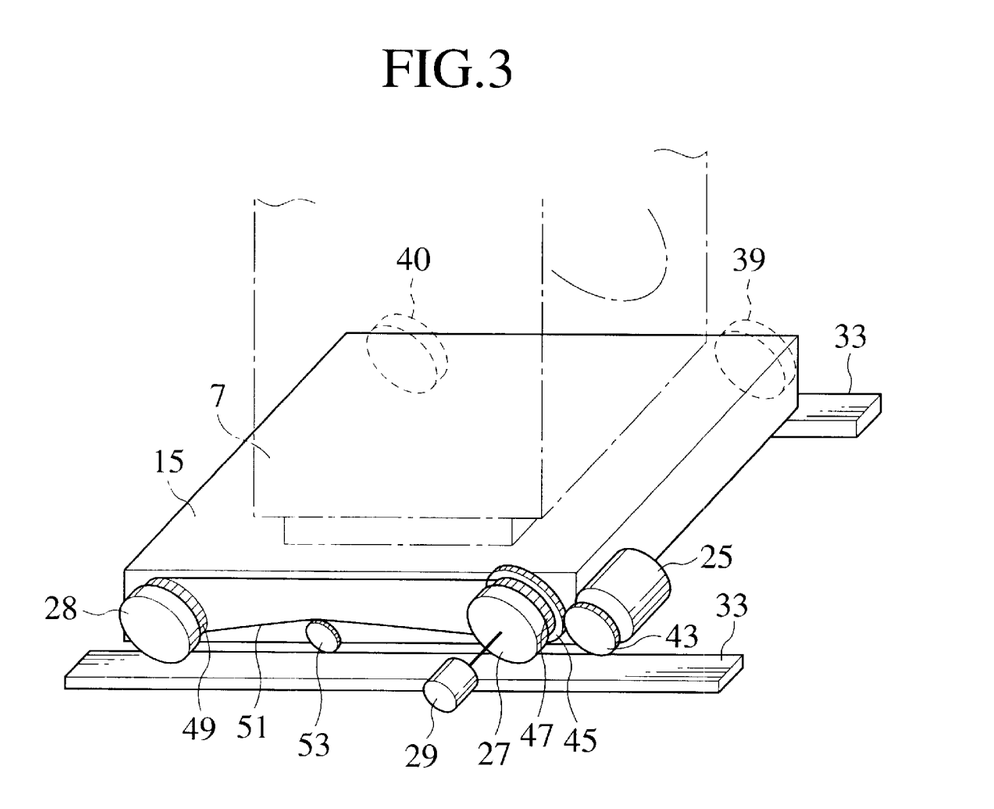
FIG. 3 is an explanatory perspective view of a moving mechanism of the X-ray CT apparatus, in accordance with a first embodiment of the present invention.

FIGS. 2 and 3 show the helical-scanning type of X-ray CT apparatus having the gantry body 7 moved with respect to the patient 5 (FIG. 1), in accordance with a first embodiment of the invention. In the figures, FIG. 2 is a block diagram for explanation of the constitution of the X-ray CT apparatus, while FIG. 3 is a perspective view of a moving arrangement of the X-ray CT apparatus.

In FIG. 2, the gantry body 7 is arranged in a radiographic room R, together with the movable dolly 15 mounting the gantry body 7 thereon. A manipulation table (console) 17 of the X-ray CT apparatus is arranged in an operation room N separated from the radiographic room through a radiation protective wall 18.

The manipulation table 17 is provided, therein, with a central processing unit (CPU) 19 which controls the whole operation of the X-ray CT apparatus. In detail, not only does the CPU 19 control respective operations of a rotating mechanism, an X-ray irradiating part, an X-ray data connecting part etc. (all not shown) in the gantry body 7, but forms an X-ray CT image of the patient 5 by the collected X-ray data to display it.

The gantry body 7 with the built-in X-ray tube 9 (FIG. 1), the built-in X-ray detector 11 (FIG. 1) and a not-shown built-in rotating mechanism for rotating the X-ray tube 9 and the X-ray detector 11 is secured on the dolly 15. As to the movement of the dolly 15, a driving unit 23 which is controlled by the CPU 19 through the intermediary of an interface (I/F) 21 electrically connected thereto, operates to rotate a drive motor 25. Then, wheels 27 are rotated by the drive motor 25, so that the dolly 15 can travel to continuously move the gantry body 7.

Upon the previous setting of a scanning area, scanning conditions etc., when the helical scanning for the object is ordered through the manipulation table 17, then the CPU 19 outputs control signals to the driving unit 23 for the drive motor 25 through the I/F 21 on the ground of the above order. Consequently, the wheels 27, 28 are rotated by the drive motor 25 to travel the dolly 15.

The dolly 15 is provided, in the vicinity of one of the wheels 27, with an encoder 29 for detecting the position of the dolly 15. In operation, the encoder 29 transmits detection signals representing the rotational angle etc. of the wheels 27, 28 to the CPU 19 through the interface 21. On the basis of the transmitted detection signals of the encoder 29, the CPU 19 verifies the difference (mating) between the ordered displacement of the dolly 19 and the actual displacement of the dolly 19 and also controls a timing of irradiating X-ray from the X-ray tube 9 and a timing of detecting the X-ray data on the X-ray detector 11 in order to accomplish the control for helical scanning.

On the frond and rear sides of the dolly 15, safety switches 31 are provided for the safety contact of the dolly 19 with a support 2 (FIG. 1) for the patient couch 1, the radiation protective wall 18 or the like. Receiving the contact signals from the safety switches 31, the I/F 21 outputs a stop signal to stop the driving of the drive motor 25.

In the modification, in place of the safety switches 31, a mat switch 32 may be provided on the upper and lower portions of the front side of the gantry body 7, as shown in FIG. 2. Note, it is preferable that these switches 31, 32 have respective sensitive parts including cushion material for softening the contact of the CT apparatus with the external objects, for example, the wall 18 and an operator.

Furthermore, the mat switch 32 may be arranged on a wall defining a radiographic port of the gantry body 7, as also shown with a dashed line of the same figure. In this case, it is expected to protect the patient 5 (FIG. 1) from coming into intense contact with the gantry body 7. Because the sensitive portion itself can absorb a time lag of generating the stop signal to the motor since the switch 32 has come into contact with the patient 5.

Additionally, in the place of the above safety switches 31, 32, the CPU 19 may control the driving unit 23 of the dolly 15 in such a manner that once the positioning of the dolly 15 prior to the helical scanning is completed, thereafter the dolly 15 can be only traveled in one direction receding from the patient 5 (FIG. 1) or the patient couch 1.

FIG. 3 shows a detailed structure of the moving arrangement of the X-ray CT apparatus. As shown in the figure, the X-ray CT apparatus is adapted so that the dolly 15 having the pair of drive wheels 27, 28 and a pair of driven wheel 39, 40 travels on rails 33 laid on a floor. The X-ray CT gantry body 7 having the X-ray tube 9, the X-ray detector 11 and the rotating mechanism accommodated therein is secured on the dolly 15 and adapted so as to continuously move in the horizontal direction, together with the dolly 15. By combining the continuous rotation of the X-ray tube 9 by the rotating mechanism with the continuous translation of the dolly 15, the X-ray CT apparatus is capable of scanning the patient (the object being scanning) in a helical manner.

As previous mentioned with reference to FIG. 2, when the helical-scanning is ordered from the manipulation table 17, then the motor 25 subjected to the control of the driving unit 23 rotates, so that the drive wheels 27, 28 are rotated through the intermediary of a drive gear 43 and a driven gear 45. The drive wheels 27, 28 synchronously rotate through the intermediary of a chain 51 bridging over chain gears 47, 49 provided on the drive wheels 27, 28, respectively. With the transmitting arrangement, the driving force is delivered to the drive wheels 27, 28, thereby preventing the drive wheel 27 from racing due to its rising from the rail 33. As a matter of course, the dolly 15 can travel on the rails 33 in succession, owing to the friction between the drive wheels 27, 28 and the rails 33, 33. Attached to an end of the drive wheel 27 is the encoder 29 which serves to inform the CPU 19 about a rotational angle of the drive wheel 27 through the I/F 21, thereby controlling the position of the gantry body 7 and the timing of helical scanning.

Note, when it is required to drive the gantry body 7 at both of high speed (e.g. positional change, rough positioning of the gantry body 7) and low speed for helical-scanning, the X-ray CT apparatus of the embodiment has only to be equipped with speed adjusting means which can adjust the rotating speed of the motor 25 by modifying any one of voltage, current, frequency, pulse frequency for the motor 25 and windings to which a power is applied.

For example, in case of using a direct current (DC) motor, the rotating speed of the motor can be modified by controlling voltage or current supplied for the motor. On the contrary, in case of using the alternating current (AC) motor, the high-speed rotation and low-speed rotation can be switched by changing the frequency of alternating current applied on the motor by means of an inverter. Similarly, in case of using a servo-motor, it is preferable to change the pulse frequency. In case of using a motor having both windings for high-speed and another windings for low-speed, it is desirable to change the winding on which the power is to be applied to another one. In this way, owing to the change in rotating speed of the motor, it is possible to switch the operation of the gantry body 7 between the high-speed moving and the low-speed moving suitable for helical-scanning.

Figure 4A:
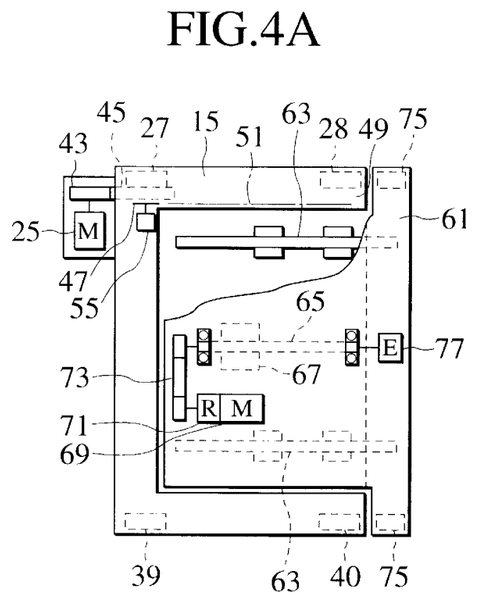
FIG. 4A is a top view of the dolly and the sliding table, FIG. 4B a side of the dolly and the sliding table.
Figure 4B:
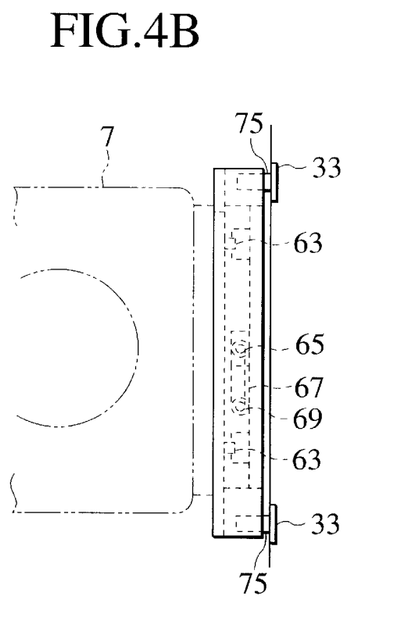
Figure 4C:
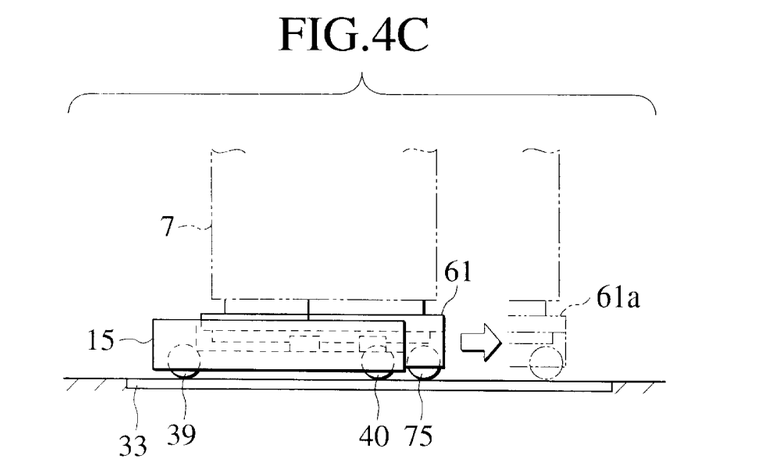
FIG. 4C is a front view of the dolly and the sliding table.

With reference to FIGS. 4A, 4B and 4C, we now describe the X-ray CT apparatus in accordance with the second embodiment. In the figures, FIG. 4A is a top view of the X-ray CT apparatus, FIG. 4B a side view of the X-ray CT apparatus, and FIG. 4C is a front view of the X-ray CT apparatus.

According to the embodiment, the X-ray CT apparatus is provided with a sliding table which allows the gantry body to be moved more precisely for the helical scanning and which is different from the dolly for positioning the gantry body.

In FIG. 4, the shown dolly 15 is constructed so as to move for changing the position by a traveling mechanism which is substantially identical to that of FIG. 3. Therefore, elements constituting the traveling mechanism are indicated with the same reference numerals of the elements of FIG. 3 and their overlapping descriptions are deleted.

The dolly 15 of the embodiment moves on the rails 33 by the traveling mechanism shown in FIG. 3. Different from the so-constructed dolly 15, a sliding table 61 mounting the gantry body 7 thereon is attached to the dolly 15 through a LM (liner moving) guide 63 as a translation guide. The front part of the sliding table 61 is born by a pair of guide wheels 75, 75 on left and right. Provided on the side of the dolly 15 is a translation driving system such as a ball screw 65 which is rotatably supported by the dolly 15 through bearings. On the other hand, a ball nut 67 is fixed to the sliding table 61.

The rotation of a motor 69 is decelerated by a reduction gear unit 71 and sequentially transmitted to the ball screw 65 by a transmission system 73 including, for example, a synchronous pulley, a synchronous belt and so on. With the arrangement, when the ball screw 65 is rotated so that the ball nut 67 is subjected to a driving force to the right hand in the figure, then the sliding table 61 is moved relatively to the dolly 15, as shown with an arrow of FIG. 4C. At this time, the drive wheels 27, 28 and the driven wheels 39, 40 are braked to a stop by a not-shown braking arrangement. Thus, the dolly 15 is at a standstill on the rails 33.

On one end of the ball screw 65, an encoder 77 is arranged to detect a rotational angle of the ball screw 65. The signal representing the rotational angle is fed to the CPU 19 (FIG. 2) via. the I/F 21 (FIG. 2). In the CPU 19, it is carried out to convert the transmitted rotational angle to a moving distance of the sliding table 61.

As the gantry body 7 is fixed on the sliding table 61, the movement of the table 61 allows the patient to be helically scanned with precision. The guide wheels 75 are subjected to load when the sliding table 61 moves forward (e.g. a position with a reference numeral 61a). Thus, according to the embodiment, owing to the provision of the sliding table 61, there is no need to extend an external form of the dolly 15 to the movement stroke of the table 61. In addition, since the sliding table 61 can be accommodated inside the dolly 15 by reverse rotating the ball screw 65, it is possible to get an accommodation space for the X-ray CT apparatus smaller, whereby it can be easily established in the operation room also requiring the CT scanning of the patient.

The third embodiment will be described with reference to FIGS. 5A and 5B as below.

According to the embodiment, the CT apparatus is provided with two driving arrangements of high-speed driving system and low-speed driving system in order to execute the helical scanning with precision. Thus, the high-speed driving system having a motor for high-speed driving is activated in the simple movement of the X-ray CT gantry, while the low-speed driving system having another motor for low-speed driving is activated in the helical scanning.

Figure 5A:
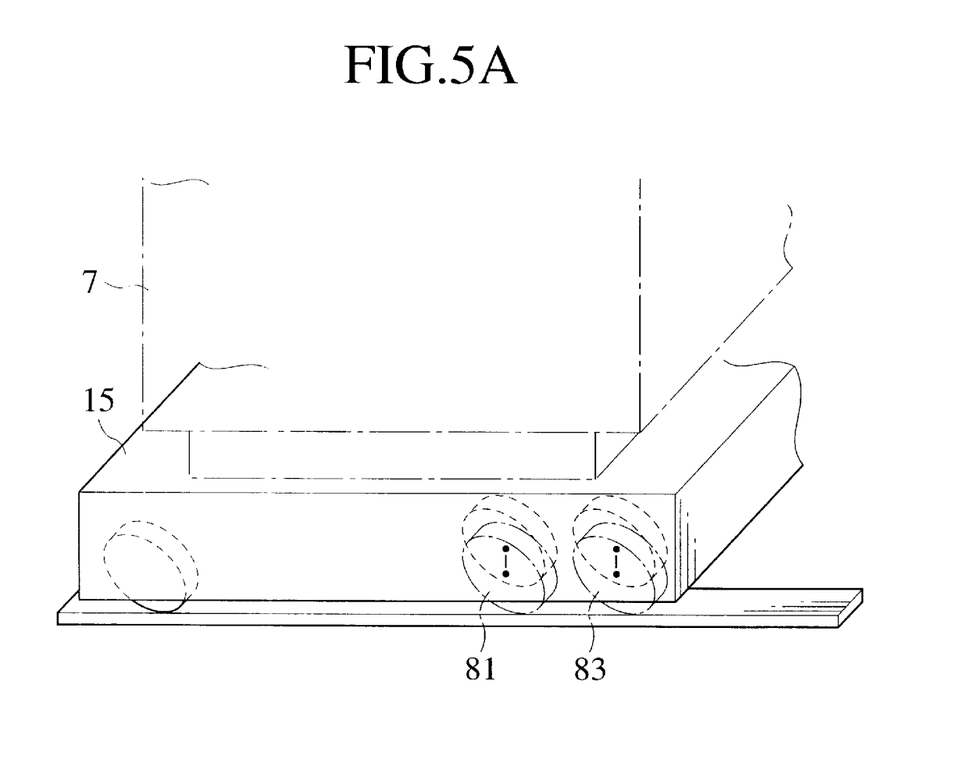
FIGS. 5A and 5B are perspective views of the X-ray CT apparatus in accordance with a third embodiment of the present invention, for explanation of the apparatus provided with a high-speed driving system and a low-speed driving system.
Figure 5B:
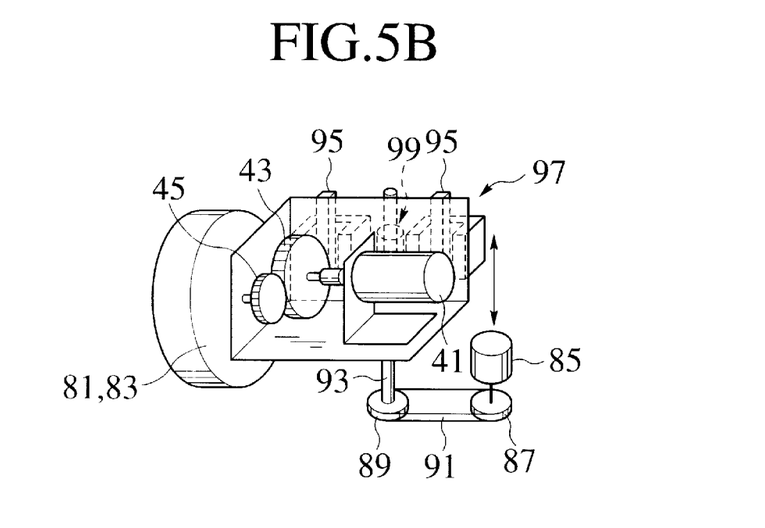

FIG. 5A is a perspective view of the dolly having both high and low-speed drive wheels. FIG. 5B is a detailed perspective view showing one of the driving systems for the high-speed drive wheels and the low-speed drive wheels and a built-in switching mechanism in the system, representatively.

The gantry body 7 rotatably carrying the not-shown X-ray tube and the X-ray detector is fixed on the dolly 15. On the underside of the dolly 15, high-speed drive wheels 81 (only one shown in the figure) and low-speed drive wheels 83 are rotatably attached so as to move in the vertical direction, respectively. In positioning the dolly 15 roughly before scanning or withdrawing the dolly 15 into the accommodation space for rest, the high-speed wheels 81 are lowered while elevating the low-speed drive wheels 83. On the contrary, for the precise movement of the dolly 15 in the helical scanning, the high-speed wheels 81 are lifted while lowering the low-speed drive wheels 83.

The mechanisms for moving the high-speed drive wheels 81 and the low-speed drive wheels 83 up and down are common with each other. That is, the dolly 15 is provided with gear boxes 97 (only one shown) each of which bears each drive wheel 81 (or 83) and includes a drive motor 41 and reduction gears 43, 45. Each gear box 97 is movably attached to the dolly 15 through the intermediary of a pair of LM (liner moving) guides 95 in the vertical direction.

For the vertical movements of the wheels 81, 83, a motor 85 is rotated at first. Then, the rotating force of the motor 85 is transmitted via. a pulley 87, a belt 91 and a pulley 89 in succession, to a ball screw 93 for rotation. Consequently, a ball nut 99 fixed on the gear box 97 is subjected to an upward or downward force, so that the switching in operations of the driving systems can be accomplished.

In a modification of the embodiment, power-cut means such as a clutch may be provided between the drive motor and the drive wheels in each driving system. In operation, when one driving system is activated by the power-cut means' operation to transmit the drive force of the motor to the wheels, then the other driving system is inactivated since the power-cut means intercepts to transmit the driving force of the motor to the wheels. Then, the wheels in the other driving system race to be the driven wheels. In such a case, it is possible to dispense with the above-mentioned vertical movement mechanisms for the wheels, whereby the switching arrangement can be simplified. In addition, since the gantry body is always supported by the drive and driven wheels in both driving systems, the stability of the X-ray CT apparatus can be improved.

As mentioned above, according to the present invention, owing to the continuous translation of the X-ray CT gantry having the rotating X-ray source, it is possible to provide the helical-scanning type of X-ray CT apparatus which is capable of executing the helical scanning without moving the object to be scanned.

Additionally, according to the invention, since the helical scanning for the object can be realized irrespective of function of feeding the tabletop of the patient couch, it is possible to accomplish the helical scanning while operating the patient with the operational table and also helical scanning during the IVR operation using a catheter bed of an angiography apparatus.

Finally, it will be understood by those skilled in the art that the foregoing description is merely related to a few of embodiments of the X-ray CT apparatus, and that various changes and modifications may be made to the present invention without departing from the spirit and scope thereof.

What is claimed is:

1. A CT apparatus for scanning an object, comprising:
    a CT gantry comprising an X-ray source configured to irradiate an X-ray while rotating about an object to be scanned and an X-ray detector configured to detect the X-ray penetrating through the object to be scanned;
    a moving unit comprising a dolly, said CT gantry being mounted on said dolly, said moving unit further comprising a driving source configured to continuously move the dolly together with the CT gantry on a floor with respect to the object to be scanned; and
    a detector configured to detect a moving distance of the CT gantry;
    whereby helical scanning of the object to be scanned can be accomplished by moving the CT gantry in succession while rotating the X-ray source about the object to be scanned.

2. The CT apparatus of claim 1, wherein
    the dolly is capable of moving in a horizontal direction; and
    wherein a rotating plane of the X-ray source is generally vertical.

3. The CT apparatus of claim 1, wherein the dolly comprises:
    a dolly body; and
    a sliding table, the CT gantry being mounted on said sliding table, and said sliding table being capable of moving continuously with respect to the dolly body.

4. A CT apparatus for scanning an object, comprising:
    a CT gantry comprising an X-ray source configured to irradiate an X-ray while rotating about an object to be scanned and an X-ray detector configured to detect the X-ray penetrating through the object to be scanned;
    a moving unit configured to continuously move the CT gantry with respect to the object to be scanned; and
    a detector configured to detect a moving distance of the CT gantry;
    wherein the moving unit comprises:
        a first driving unit configured to position the CT gantry in a rough-and-ready manner;
        a second driving unit configured to move the CT gantry strictly for helical-scanning; and
        a switching unit configured to switch operations of the first and second driving units so that either one of the first and second driving units operates solely;
    whereby helical scanning of the object to be scanned can be accomplished by moving the CT gantry in succession while rotating the X-ray source about the object to be scanned.

5. The CT apparatus of claim 1, wherein the moving unit comprises:
   a single drive motor as the driving source; and
   a changing unit configured to change a rotating speed of the single drive motor by changing any one of voltages, currents, frequency, pulse frequency all supplied for the single drive motor and motor windings to which power is applied.

6. A CT apparatus for scanning an object, comprising:
   a CT gantry comprising an X-ray source configured to irradiate an X-ray while rotating about an object to be scanned and an X-ray detector configured to detect the X-ray penetrating through the object to be scanned, a rotating plane, of the X-ray source being generally vertical;
   a moving unit configured to continuously move the CT gantry with respect to the object to be scanned, the moving unit having a dolly on which the CT gantry is mounted and being capable of moving in a horizontal direction, wherein the dolly is provided with at least one safety switch configured to detect that the dolly comes into contact with an external object which is not a constituent of the X-ray CT apparatus; and
   a detector configured to detect a moving distance of the CT gantry;
   whereby helical scanning of the object to be scanned can be accomplished by moving the CT gantry in succession while rotating the X-ray source about the object to be scanned.

7. A CT apparatus for scanning an object, comprising:
   a CT gantry comprising an X-ray source configured to irradiate an X-ray while rotating about an object to be scanned and an X-ray detector configured to detect the X-ray penetrating through the object to be scanned, a rotating plane of the X-ray source being generally vertical;
   a moving unit configured to continuously move the CT gantry with respect to the object to be scanned, the moving unit having a dolly on which the CT gantry is mounted and being capable of moving in a horizontal direction; and
   a detector configured to detect a moving distance of the CT gantry;
   wherein the CT gantry is provided, on a front side thereof close to the object to be scanned, with at least one safety switch configured to detect that the CT gantry comes into contact with an external object which is not a constituent of the X-ray CT apparatus;
   whereby helical scanning of the object to be scanned can be accomplished by moving the CT gantry in succession while rotating the X-ray source about the object to be scanned.

8. A CT apparatus for scanning an object, comprising:
   a CT gantry comprising an X-ray source configured to irradiate an X-ray while rotating about an object to be scanned and an X-ray detector configured to detect the X-ray penetrating through the object to be scanned, a rotating plane of the X-ray source being generally vertical;
   a moving unit configured to continuously move the CT gantry with respect to the object to be scanned, the moving unit having a dolly on which the CT gantry is mounted and being capable for moving in a horizontal direction; and
   a detector configured to detect a moving distance of the CT gantry;
   wherein the CT gantry is provided, on an inner wall defining a radiographic port thereof, with a safety switch configured to detect that the CT gantry comes into contact with the object to be scanned;
   whereby helical scanning of the object to be scanned can be accomplished by moving the CT gantry in succession while rotating the X-ray source about the object to be scanned.

9. The CT apparatus of claim 8, wherein the safety switch is in form of a mat switch of which sensitive part includes material configured to cushion the object to be scanned against a contact thereof with the CT gantry.

10. The CT apparatus of claim 2, wherein the moving unit further comprises a control unit configured to control the dolly in such a manner that once the positioning of the dolly prior to the helical scanning is completed, thereafter the dolly can be only traveled in one direction receding from the object to be scanned.

* * * * *